United States Patent [19]
Hötten et al.

[11] Patent Number: 5,994,094
[45] Date of Patent: Nov. 30, 1999

[54] GROWTH/DIFFERENTIATION FACTOR OF THE TGF-β FAMILY

[75] Inventors: Gertrud Hötten, Bammental; Helge Neidhardt, Marburg; Michael Paulista, Leimen, all of Germany

[73] Assignee: Biopharm Gesellschaft Zur Biotechnologischen, Heidelberg, Germany

[21] Appl. No.: 08/288,508

[22] Filed: Aug. 10, 1994

[30] Foreign Application Priority Data

Aug. 10, 1993 [DE] Germany ............................. 43 268 29
May 25, 1994 [DE] Germany ............................. 44 182 22
Jun. 9, 1994 [DE] Germany ............................. 44 201 57

[51] Int. Cl.$^6$ .......................... C12P 21/00; C12N 15/00; C07H 21/04
[52] U.S. Cl. .................... 435/69.1; 435/69.4; 435/320.1; 435/252.3; 435/254.11; 435/325; 536/23.5
[58] Field of Search ................................ 435/69.4, 320.1, 435/252.3, 254.11; 536/23.5; 436/69.1

[56] References Cited

U.S. PATENT DOCUMENTS 5,266,683  11/1993  Opermann et al. .................... 530/326
5,801,014   9/1998  Lee et al. ............................... 435/69.1

FOREIGN PATENT DOCUMENTS

WO 90/11366  10/1990  WIPO.
WO 91/05802   5/1991  WIPO.
WO 93/16099   8/1993  WIPO.
WO 94/15949   7/1994  WIPO.

OTHER PUBLICATIONS

Sambrook et al. Molecular Cloning: A Laboratory Manual Second Edition vol. 1,2 and 3. Cold Spring Harbor Laboratory Press: Cold Spring Harbor, New York, U.S.A. Nov. 1989.

Storm et al. Nature 368, 639–643, 1994.

*Primary Examiner*—Elizabeth Kemmerer
*Assistant Examiner*—David S. Romeo
*Attorney, Agent, or Firm*—Nikaido Marmelstein Murray & Oram, LLP

[57] ABSTRACT

The invention concerns a protein of the TGF-β family, the DNA coding therefor and a pharmaceutical composition containing the protein.

10 Claims, 7 Drawing Sheets

Fig.1a

|  | 10 | 20 | 30 | 40 | 50 |
|---|---|---|---|---|---|
| SEQ ID NO 13 MP 52 | CSRKALHVNF | KDMGWDDWII | APLEYEAFHC | EGLCEFPLRS | HLEPTNHAVI |
| SEQ ID NO 14 BMP 2 | CKRHPLYVDF | SDVGWNDWIV | APPGYHAFYC | HGECPFPLAD | HLNSTNHAIV |
| SEQ ID NO 15 BMP 4 | CRRHSLYVDF | SDVGWNDWIV | APPGYQAFYC | HGDCPFPLAD | HLNSTNHAIV |
| SEQ ID NO 16 BMP 5 | CKKHELYVSF | RDLGWQDWII | APEGYAAFYC | DGECSFPLNA | HMNATNHAIV |
| SEQ ID NO 17 BMP 6 | CRKHELYVSF | QDLGWQDWII | APKGYAANYC | DGECSFPLNA | HMNATNHAIV |
| SEQ ID NO 18 BMP 7 | CKKHELYVSF | RDLGWQDWII | APEGYAAYYC | EGECAFPLNS | YMNATNHAIV |
|  | * + * * | * *** ****+ | ** * * *+ * | +* * *** * | ++ **** |

Fig.1

| Fig.1a | Fig.1b |
|---|---|

Fig.1b

|  | 60 | 70 | 80 | 90 | 100 |  |
|---|---|---|---|---|---|---|
| SEQ ID NO 13 MP 52 | QTLMNSMDPE | STPPTCCVPT | RLSPISILFI | DSANNVVYKQ | YEDMVVESCG | CR |
| SEQ ID NO 14 BMP 2 | QTLVNSVNS- | KIPKACCVPT | ELSAISMLYL | DENEKVVLKN | YQDMVVEGCG | CR |
| SEQ ID NO 15 BMP 4 | QTLVNSVNS- | SIPKACCVPT | ELSAISMLYL | DEYDKVVLKN | YQEMVVEGCG | CR |
| SEQ ID NO 16 BMP 5 | QTLVHLMFPD | HVPKPCCAPT | KLNAISVLYF | DDSSNVILKK | YRNMVVRSCG | CH |
| SEQ ID NO 17 BMP 6 | QTLVHLMNPE | YVPKPCCAPT | KLNAISVLYF | DDNSNVILKK | YRNMVVRACG | CH |
| SEQ ID NO 18 BMP 7 | QTLVHFINPE | TVPKPCCAPT | QLNAISVLYF | DDSSNVILKK | YRNMVVRACG | CH |
|  | *** +++ ++ | +* ****+* | *+ *** * | * +++ * | * +**++ | ** |

Fig.2a

```
                              Eco RI  Nco I
SEQ ID NO 19  OD     ATGAATTCCCATGGACCTGGGCTGGMAKGAMTGGAT
SEQ ID NO 20  BMP 2                  ACGTGGGGTGGAATGACTGGAT
SEQ ID NO 21  BMP 3                  ATATTGGCTGGAGTGAATGGAT
SEQ ID NO 22  BMP 4                  ATGTGGGCTGGAATGACTGGAT
SEQ ID NO 23  BMP 7                  ACCTGGGCTGGCAGGACTGGAT
SEQ ID NO 24  TGF-β1                 AGGACCTCGGCTGGAAGTGGAT
SEQ ID NO 25  TGF-β2                 GGGATCTAGGGTGGAAATGGAT
SEQ ID NO 26  TGF-β3                 AGGATCTGGGCTGGAAGTGGGT
SEQ ID NO 27  INHIBIN α              AGCTGGGCTGGGAACGGTGGAT
SEQ ID NO 28  INHIBIN βA             ACATCGGCTGGAATGACTGGAT
SEQ ID NO 29  INHIBIN βB             TCATCGGCTGGAACGACTGGAT
```

Fig.2b

```
                              Eco RI
SEQ ID NO 30  OID    ATGAATTCGAGCTGCGTSGGSRCACAGCA
SEQ ID NO 31  BMP 2              GAGTTCTGTCGGGACACAGCA
SEQ ID NO 32  BMP 3              CATCTTTTCTGGTACACAGCA
SEQ ID NO 33  BMP 4              CAGTTCAGTGGGCACACAACA
SEQ ID NO 34  BMP 7              GAGCTGCGTGGGCGCACAGCA
SEQ ID NO 35  TGF-β1             CAGCGCCTGCGGCACGCAGCA
SEQ ID NO 36  TGF-β2             TAAATCTTGGGACACGCAGCA
SEQ ID NO 37  TGF-β3             CAGGTCCTGGGGCACGCAGCA
SEQ ID NO 38  INHIBIN α          CCCTGGGAGAGCAGCACAGCA
SEQ ID NO 39  INHIBIN βA         CAGCTTGGTGGGCACACAGCA
SEQ ID NO 40  INHIBIN βB         CAGCTTGGTGGGAATGCAGCA
```

GROWTH/DIFFERENTIATION FACTOR OF THE TGF-β FAMILY

The present invention concerns a new growth/differentiation factor of the TGF-β family and DNA sequences coding therefor.

The TGF-β family of growth factors which includes BMP-, TGF- and inhibin-related proteins (Roberts and Sporn, Handbook of Experimental Pharmacology 95 (1990), 419–472) is particularly relevant for a wide range of medical treatment methods and applications. These factors are suitable in methods which concern wound-healing and tissue regeneration. Furthermore several members from the TGF-β family induce tissue growth, in particular growth of bones, and therefore play a crucial role in inducing the development of cartilage and bones.

Wozney (Progress in Growth Factor Research 1 (1989), 267–280) and Vale et al (Handbook of Experimental Pharmacology 95 (1990), 211–248) describe various growth factors such as those which are related to the BMP group (bone morphogenetic proteins) and the inhibin group. The members of these groups show significant structural similarities. The precursor of the protein consists of an amino-terminal signal sequence, a propeptide and a carboxy-terminal sequence of about 110 amino acids that are cleaved from the precursor and constitute the mature protein. In addition their members are defined by an amino acid sequence homology. The mature protein contains the most conserved sequences, in particular seven cysteine residues which are conserved among the family members. The TGF-β-like proteins are multifunctional, hormonally active growth factors. They also have related biological activities such as chemotactic attraction of cells, promotion of cell differentiation and tissue-inducing capabilities such as cartilage-inducing and bone-inducing capabilities. The U.S. Pat. No. 5,013,649 discloses DNA sequences that code for osteo-inductive proteins that are denoted BMP-2 and the U.S. patent applications Ser. No. 179 101 and 170 197 disclose the BMP proteins BMP-1 and BMP-3. Moreover many types of cells are able to synthesize TGF-β-like proteins and practically all cells have TGF-β receptors.

On the whole these proteins show differences in their structure which leads to significant variations in their exact biological function. In addition they are found in a wide range of different types of tissue and at various stages of development. As a result they can exhibit differences with regard to their exact function e.g. the required cellular physiological environment, their life-span, their target sites, their requirements for auxiliary factors and their stability against degradation. Thus, although a multitude of proteins have been described that exhibit a tissue-inductive and in particular osteo-inductive potential, their natural functions in the organism and—more significantly—their medical relevance still have to be investigated in detail. It is thought to be highly probable that members of the TGF-β family are present that are still unknown which are important for osteogenesis or the differentiation/induction of other types of tissue. A major difficulty in the isolation of these new TGF-β-like proteins is, however, that their functions cannot yet be described exactly enough to develop highly discriminating bioassays. On the other hand the expected nucleotide sequence homology to other members of the family is too low to enable a screening by classical nucleic acid hybridization techniques. Nevertheless the further isolation and characterization of new TGF-β-like proteins is urgently required in order to provide further inducing and differentiation-promoting proteins that fulfil all the desired medical requirements. These factors could be used medically in the healing of lesions and the treatment of degenerative diseases of bones and/or other types of tissue such as the kidney or the liver.

A nucleotide and amino acid sequence for the TGF-β protein MP-52 is stated in the Patent Application PCT/EP93/00350 in which the sequence corresponding to the mature peptide and a major portion of the sequence corresponding to the propeptide of MP-52 are given. The complete sequence of the propeptide MP-52 is not disclosed.

The object on which the present invention is based is to provide DNA sequences that code for new members of the TGF-β protein family with mitogenic and/or differentiation-inductive e.g. osteo-inductive potential. The object of the present invention was therefore in particular to provide the complete DNA and amino acid sequence of the TGF protein MP-52.

This object is achieved by a DNA molecule that codes for a protein of the TGF-β family and which comprises (a) the part coding for the mature protein and if desired further functional parts of the nucleotide sequence shown in SEQ ID NO. 1, (b) a nucleotide sequence corresponding to a sequence from (a) within the scope of the degeneracy of the genetic code, (c) an allelic derivative of a nucleotide sequence corresponding to one of the sequences from (a) and (b) or (d) a sequence hybridizing with one of the sequences from (a), (b) or (c) provided that a DNA molecule according to (d) contains at least the part coding for a mature protein from the TGF-β family.

Further embodiments of the present invention concern the subject matter of claims 2 to 10. Other features and advantages of the invention can be derived from the description of the preferred embodiments and figures. The sequence protocols and figures are now briefly described.

SEQ ID NO. 1 shows the complete nucleotide sequence of the DNA coding for the TGF-β protein MP-52. The ATG start codon starts with nucleotide 640. The start of the mature protein begins after nucleotide 1782.

SEQ ID No. 2 shows the complete amino acid sequence of the TGF-β protein MP-52 which was derived from the nucleotide sequence shown in SEQ ID NO. 1.

FIG. 1 shows a comparison between the amino acid sequence of MP-52 and several members of the BMP protein family starting with the first of the seven conserved cysteine residues. * denotes that the amino acid is the same in all compared proteins; + denotes that the amino acid corresponds in at least one of the proteins compared to MP-52.

FIG. 2 shows the nucleotide sequences of the oligonucleotide primers that were used in the present invention and a comparison of these sequences with known members of the TGF-β family. M denotes A or C, S denotes C or G, R denotes A or G and K denotes G or T. 2a shows the sequence of the primer OD, 2b shows the sequence of the primer OID.

Figure 3:
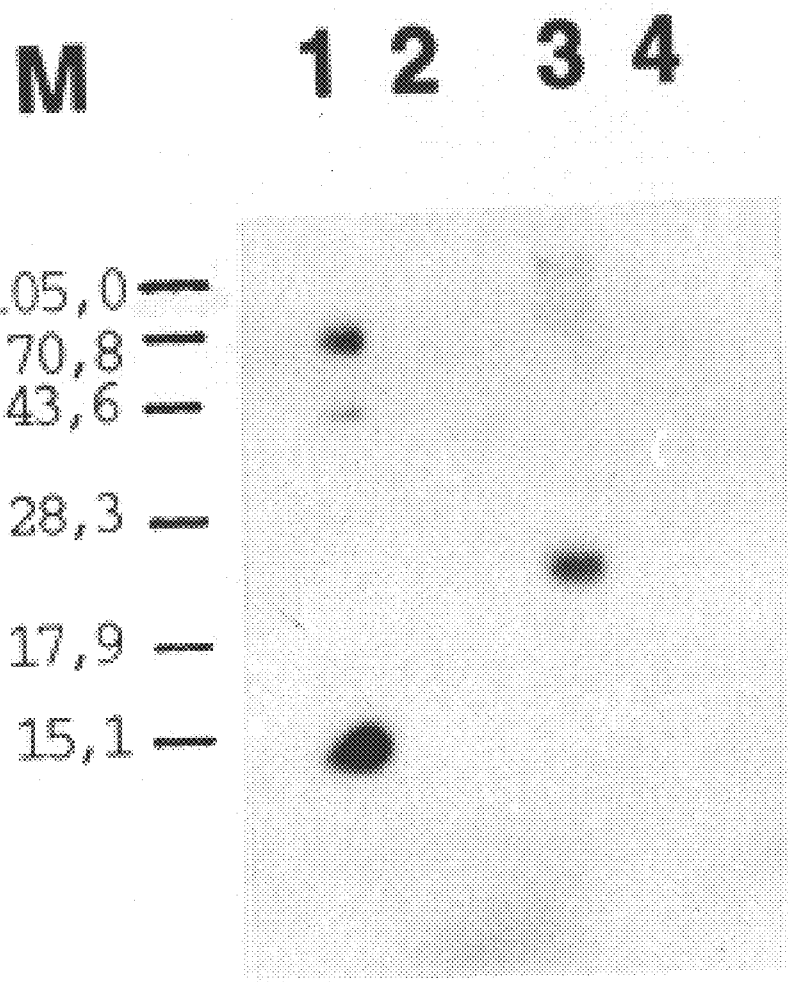

The present invention encompasses at least the part coding for the mature protein and if desired further functional parts of the nucleotide sequence shown in SEQ ID NO. 1 as well as sequences that correspond to this sequence within the scope of the degeneracy of the genetic code and allelic derivatives of such sequences. In addition the present invention also encompasses sequences that hybridize with such sequences provided that such a DNA molecule completely contains at least the part coding for the mature protein of the TGF-β family.

The term "functional part" within the sense of the present invention denotes a protein part which is capable of acting for example as a signal peptide, propeptide or as a mature protein part i.e. it fulfils at least one of the biological functions of the natural protein parts of MP-52.

The region coding for the mature part of the protein extends from nucleotides 1783–2142 of the sequence shown in SEQ ID NO. 1. If desired, the DNA molecule can also comprise further functional parts of the sequence shown in SEQ ID NO. 1, namely the nucleotide sequences coding for the signal or/and propeptide part. It is particularly preferred that the DNA molecule comprises the sequence for the signal and the propeptide part and the part of the mature protein i.e. nucleotides 640–2142 of the sequence shown in SEQ ID NO. 1. On the other hand the DNA molecule can also comprise functional signal or/and propeptide parts from other proteins in addition to the part coding for the mature protein, in particular from other proteins of the TGF-β family e.g. the above-mentioned BMP proteins. The respective nucleotide sequences are given in the references mentioned above to the disclosure of which reference is hereby being made.

Moreover the present invention also encompasses a DNA molecule as defined above that contains a non-coding intron sequence between nucleotides 1270 and 1271 of the sequence shown in SEQ ID NO. 1. This intron sequence is contained in the plasmid SKL 52 (H3) MP12 which is deposited at the DSM and has the genomic nucleic acid sequence of MP-52.

The invention also encompasses the cDNA sequence of the MP-52 protein coded by the phage λ 15.1. This sequence starts with nucleotide 321 of SEQ ID NO. 1.

Although the allelic, degenerate and hybridizing sequences which are encompassed by the present invention have structural differences due to slight changes in their nucleotide or/and amino acid sequence, the proteins coded by such sequences still essentially have the same useful properties that enable their use in basically the same medical applications.

The term "hybridization" according to the present invention means the usual hybridization conditions, preferably conditions with a salt concentration of 6×SSC at 62 to 66° C. followed by a one hour wash with 0.6×SSC, 0.1% SDS at 62 to 66° C. It is particularly preferred that the term "hybridization" denotes stringent hybridization conditions with a salt concentration of 4×SSC at 62 to 66° C. followed by a one hour wash with 0.1×SSC, 0.1% SDS at 62 to 66° C.

Preferred embodiments of the present invention are DNA sequences as defined above that are obtainable from vertebrates, preferably mammals such as pigs, cows and rodents such as rats or mice and in particular from primates such as humans.

A particularly preferred embodiment of the present invention is the sequence denoted MP-52 shown in SEQ ID NO. 1. The transcripts of MP-52 were obtained from embryonic tissue and code for a protein which has a considerable amino acid homology to the mature portion of BMP-like proteins (see FIG. 1). The protein sequences of BMP2 (=BMP2A) and BMP4 (=BMP2B) are described by Wozney et al., Science 242 (1988), 1528–1534. The corresponding sequences of BMP5, BMP6 and BMP7 are described by Celeste et al., Proc. Natl. Acad. Sci. USA 87 (1990), 9843–9847. Several typical sequence homologies which are specific for known BMP sequences have also been found in the propeptide part of MP-52 whereas other parts of the precursor part of MP-52 exhibit considerable differences to BMP precursors.

In addition the present invention concerns a vector that contains at least one copy of a DNA molecule according to the invention. The DNA sequence according to the invention is preferably operatively linked to an expression control sequence in such a vector. Such vectors are suitable for the production of TGF-β-like proteins in stably or transiently transformed cells. Various animal, plant, fungal and bacterial systems can be used for the transformation and subsequent culture. The vectors according to the invention preferably contain sequences necessary for replication in the host cell and are autonomously replicable. Furthermore the use of vectors is preferred that contain selectable marker genes which can be used to detect transformation of a host cell.

In addition the invention concerns a host cell which is transformed with a DNA according to the invention or with a vector according to the invention. Examples of suitable host cells include various eukaryotic and prokaryotic cells such as *E. coli*, insect cells, plant cells, mammalian cells and fungi such as yeast.

In addition the invention concerns a protein of the TGF-β family which is coded by a DNA sequence according to claim 1. The protein according to the invention preferably has the amino acid sequence shown in SEQ ID NO. 2 or if desired functional parts thereof and exhibits biological properties such as tissue-inductive in particular osteo-inductive or/and mitogenic capabilities that may be relevant for a therapeutic application. The above-mentioned characteristics of the protein can vary depending on the formation of homodimers or heterodimers. Such structures may also prove to be suitable for clinical applications.

The biological properties of the proteins according to the invention, in particular the mitogenic and osteo-inductive potential can be determined for example in assays according to Seyedin et al., PNAS 82 (1985), 2267–2271 or Sampath and Reddi, PNAS 78 (1981), 7599–7603.

Furthermore the present invention concerns a process for the production of a protein of the TGF-β family which is characterized in that a host cell transformed with a DNA according to the invention or with a vector according to the invention is cultured and the TGF-β protein is isolated from the cell or/and culture supernatant. Such a process comprises culturing the transformed host cell in a suitable culture medium and purifying the TGF-β-like protein produced. In this manner the process enables the production of an adequate amount of the desired protein for use in medical treatment or in applications using cell culture techniques which require growth factors. The host cell can be a bacterium such as Bacillus or *E. coli*, a fungus such as yeast, a plant cell such as tobacco, potato or arabidopsis or an animal cell and in particular a vertebrate cell line such as MOCOS or CHO cell lines or an insect cell line.

Yet another subject matter of the present invention is the provision of pharmaceutical compositions which contain a pharmaceutically active amount of a TGF-β-like protein according to the invention as the active substance. If desired, such a composition comprises a pharmaceutically acceptable carrier substance, auxiliary substance, diluent or filler. Such a pharmaceutical composition can be used in wound-healing and tissue regeneration as well as in the healing of damage to bones, cartilage, connective tissue, skin, mucous membranes, epithelium or teeth and in dental implants either alone or in combination with other active substances e.g. other proteins of the TGF-β family or growth factors such as EGF (epidermal growth factor) or PDGF (platelet derived growth factor). Moreover such a pharmaceutical composition can be used in the prevention of diseases such as the prevention of osteoporosis and arthrosis.

Another possible clinical application of the TGF-β protein according to the invention is to use it as a suppressor of an immunoreaction to prevent rejection of organ transplants or its application in connection with angiogenesis. The pharmaceutical composition according to the invention can also be used prophylactically or in cosmetic surgery. In addition administration of the composition is not limited to humans but can also encompass animals and in particular pets.

Finally the present invention also concerns an antibody that binds specifically to the proteins according to the invention or such an antibody fragment (e.g. Fab or Fab'). Processes for the production of such a specific antibody or antibody fragment are part of the general technical knowledge of an average person skilled in the art. Such an antibody is preferably a monoclonal antibody. Such antibodies or antibody fragments may also be suitable for diagnostic methods.

It is intended to elucidate the invention further by the following example.

EXAMPLE 1

Isolation of MP-52

1.1 Total RNA was isolated from human embryonic tissue (8 to 9 weeks old) according to the method of chirgwin et al., Biochemistry 18 (1979), 5294–5299. Poly(A+) RNA was separated from the total RNA by oligo (dT) chromatography according to the manufacturer's instructions (Stratagene Poly (A) Quick columns).

1.2 For the reverse transcription reaction 1 to 2.5 μg poly (A+) RNA was heated for 5 minutes to 65° C. and quickly cooled on ice. The reaction mixture contained 27 U RNA-Guard (Pharmacia), 2.5 μg oligo (dT)12–18 (Pharmacia), 5xbuffer (250 mmol/l Tris/HCl, pH 8.5, 50 mmol/l MgCl$_2$, 50 mmol/l DTT, 5 mmol/l of each dNTP, 600 mmol/l KCl) and 20 U AMV reverse transcriptase (Boehringer Mannheim) per μg poly (A+) RNA. The reaction mixture (25 μl) was incubated for 2 hours at 42° C.

1.3 The deoxynucleotide primers OD and OID shown in FIG. 2 were prepared on an automatic DNA synthesizer (Biosearch). The purification was carried out by denaturing polyacrylamide gel electrophoresis and isolating the main bands from the gel by means of isotachophoresis. The oligonucleotides were designed by comparing the nucleic acid sequences of known members of the TGF-β family and selecting regions with the highest conservation. A comparison of this region is shown in FIG. 2. In order to facilitate cloning both nucleotides contained EcoRI restriction sites and OD additionally contained a NcoI restriction site at its 5' terminus.

1.4 cDNA corresponding to 20 ng poly (A+) RNA was used as the starting material in the PCR reaction. The reaction was carried out in a volume of 50 μl and contained 1xPCR buffer (16.6 mmol/l (NH$_4$)$_2$SO$_4$, 67 mmol/l Tris/HCl pH 8.8, 2 mmol/l MgCl$_2$, 6.7 μmol/l EDTA, 10 mmol/l β-mercapto-ethanol, 170 μg/ml bovine serum albumin (Gibco), 200 μmol/l of each dNTP (Pharmacia), 30 pmol of each oligonucleotide (OD and OID) and 1.5 U Taq polymerase (AmpliTaq, Perkin Elmer Cetus). The reaction mixture was overlayed with paraffin and 40 PCR cycles were carried out. The products of the PCR reaction were purified by phenol/chloroform extraction and concentrated by ethanol precipitation.

1.5 The PCR reaction product was cleaved with the restriction enzymes SphI (Pharmacia) and AlwNI (Biolabs) according to the manufacturer's instructions.

1.6 The products of the restriction cleavage were fractionated by Agarose gel electrophoresis. After staining with ethidium bromide, uncleaved amplification products were cut out of the gel and isolated by phenol extraction. The DNA obtained was subsequently purified twice by phenol/chloroform extraction.

1.7 After an ethanol precipitation, a quarter or a fifth of the isolated DNA was reamplified using the same conditions as for the primary amplification except that the number of cycles was reduced to 13. The reamplification products were purified, cleaved with the same enzymes as above and the uncleaved products were isolated from Agarose gels as elucidated above for the amplification products. The reamplification step was repeated twice.

1.8 After the last isolation from the gel, the amplification products were cleaved by 4 units EcoRI (Pharmacia) under the conditions recommended by the manufacturer. A fourth of the restriction mixture was ligated into the vector pBluescriptII SK+ (Stratagene) cleaved with EcoRI. 24 clones were analysed further by means of sequencing after ligation. The sample cleaved with AlwNI and SphI resulted in a new sequence that was denoted MP-52. The other clones mainly contained BMP6 sequences and one contained a BMP7 sequence.

The clone was completed up to the 3' end of the cDNA according to the method described in detail by Frohmann (Amplifications, published by Perkin-Elmer Corp., Issue 5 (1990), pp 11–15). The same embryonic mRNA that had been used to isolate the first fragment of MP-52 was reversally transcribed as described above. The amplification was carried out using the adapter primer [SEQ ID NO. 3] (AGAATTCGCATGCCATGGTCGACG) and an internal primer [SEQ ID NO. 4] (CTTGAGTACGAGGCTTTCCACTG) of the MP-52 sequence. The amplification products were reamplified using an overlapping adapter primer (ATTCGCATGCCATGGTCGACGAAG) [SEQ ID NO. 5] and an overlapping internal primer [SEQ ID NO. 6] (GGAGCCCACGAATCATGCAGTCA) of the MP-52 sequence. After restriction cleavage with NcoI the reamplification products were cloned and sequenced into a vector that was cleaved in the same way (pUC 19 (Pharmacia No. 27-4951-01) having a modified multiple cloning site which contains a single NcoI restriction site) and sequenced. The clones were characterized by their sequence overlapping at the 3' end of the known MP-52 sequence. One of these was used as a probe to screen a human genomic gene bank (Stratagene No. 946203) according to a method described in detail by Ausubel et al. (Current Protocols in Molecular Biology, published by Greene Publishing Associates and Wiley-Interscience (1989)). One phage (λ2.7.4) was isolated from 8×10$^5$ λ phages which contained an insertion of about 20 kb and which is deposited at the DSM under the depository number 7387. This clone contains further sequence informations at the 5' end in addition to the sequence isolated from MRNA by the described amplification methods.

For the sequence analysis a HindIII fragment of about 7.5 kb was subcloned into a vector cleaved in the same manner (Bluescript SK, Stratagene No. 212206). This plasmid denoted SKL 52 (H3) MP12 was also deposited at the DSM under the depository number 7353. The sequence information shown in SEQ ID NO. 1 was derived from the phage λ 2.7.4. The ATG at position 640 is the first ATG within the reading frame (a stop codon occurs at position 403). Based on the sequence data it may be assumed that this is the start codon for the translation.

The genomic DNA contains an intron of about 2 kb between base pairs 1270 and 1271 of SEQ ID NO. 1. The sequence of the intron is not shown. The correctness of the splicing site was confirmed by sequencing an amplification product which was derived from cDNA containing this region. These sequence informations were obtained using a slightly modified method which is described in detail by Frohmann (Amplifications, published by Perkin-Elmer Corporation, Issue 5 (1990), pp 11–15). The same embryonic RNA that was also used to isolate the 3' end of MP-52 was reverse transcribed using an internal primer orientated in the 5' direction of the MP-52 sequence (ACAGCAGGTGGGTGGTGTGGACT) [SEQ ID NO. 7]. A polyA tail was attached to the 5' end of the first cDNA strand using terminal transferase. A two-step amplification was carried out, firstly by using a primer composed of oligo dT and an adapter sequence [SEQ ID NO. 8] (AGAATTCGCATGCCATGGTCGACGAAGC(T16)) and secondly an adapter primer [SEQ ID NO. 3] (AGAATTCGCATGCCATGGTCGACG) and an internal primer [SEQ ID NO. 9] (CCAGCAGCCCATCCTTCTCC) from the MP-52 sequence. The amplification products were reamplified using the same adapter primer and an overlapping internal primer [SEQ ID NO. 10] (TCCAGGGCACTAATGTCAAACACG) from the MP-52 sequence. Subsequently the reamplification products were reamplified using an overlapping adapter primer [SEQ ID NO. 5] (ATTCGCATGCCATGGTCGACGAAG) and an overlapping internal primer [SEQ ID NO. 11] (ACTAATGTCAAACACGTACCTCTG) from the MP-52 sequence. The final reamplification products were cloned with blunt ends into a vector (Bluescript SK, Stratagene No. 212206) which had been cleaved with EcoRV. The clones were characterized by their sequence overlapping with the DNA of λ 2.7.4.

In addition a cDNA bank—produced from RNA of human fibroblasts and cloned into λgt10—was screened. In this process 2×10⁶ phages were tested using a ca. 1 kb fragment of genomic MP-52 DNA (2nd exon up to the HindIII restriction site in the 3' untranslated region) as a radioactive probe. 17 mixed plaques were picked out and were checked by PCR using primers from the 5' and 3' region of the MP-52 sequence. Subsequently 8 phage plaques were selected and isolated. CDNA was isolated from the phage by an EcoRI partial cleavage and cloned into the Bluescript vector that was also cleaved with EcoRI.

Sequencing of one of the resulting plasmids SK52L15.1MP25 showed that the longest phage (15.1) starts at nucleotide No. 321 of SEQ ID NO. 1. In addition the splicing position (nucleotide 1270) was confirmed by the sequencing.

The plasmid SKL 52 (H3) MP12 was deposited on Dec. 10th 1992 at the DSM ("Deutsche Sammlung von Mikroorganismen und Zellkulturen, Mascheroder Weg 1b, 38124 Braunschweig) under the depository number 7353.

The phage λ 2.7.4 was deposited on Jan. 13th 1993 at the DSM under the depository number 7387.

The plasmid SK52L15.1MP25 was deposited on Jul. 16th 1993 at the DSM under the depository number 8421.

EXAMPLE 2

Expression of MP52

Various systems were checked for the expression of MP52. The use of Vaccinia viruses as an expression system is described in detail and capable of being reproduced by a person skilled in the art in Current Protocols in Molecular Biology (Ausubel et al., Greene Publishing Associates and Wiley-Interscience, Wiley & Sons), abbreviated CP in the following, in chapter 16 unit 16.15–16.18. The system is based on the fact that foreign DNA can be integrated by homologous recombination into the genome of the Vaccinia virus using certain vectors. For this purpose the vector used contains the TK (thymidine kinase) gene from the Vaccinia genome. In order to enable selection for recombinant viruses the vector in addition contains the E. coli xanthine-guanine phosphoribosyl transferase gene (gpt) (Falkner et al., J. Virol. 62 (1988), 1849–1854). The CDNA with the entire region coding for MP52 was cloned into this vector. The cDNA comes from plasmid SK52L15.1MP25 (DSM, depository number 8421) which was, however, firstly deleted and subcloned in order to remove a large portion of the 5' untranslated region. For this the plasmid SK52L15.1MP25 was linearized with SalI and the 5' end was deleted stepwise with the ExoIII/mung bean kit (Stratagene #200330) according to the manufacturer's instructions. After restriction with BamHI, the MP52 cDNAs that had been deleted to different extents were separated from the residual vector and isolated by an agarose gel and subcloned (pSK52s) according to standard methods (Sambrook et al., Molecular Cloning, second edition, Cold Spring Harbor Laboratory Press 1989) in a pBluescriptII SK vector (Stratagene #212206) restricted with EcoRV and BamHI. All restrictions were carried out according to the manufacturer's instructions. Sequencing with Sequenase (USB/Amersham #70770) yielded inter alia a clone which starts with nucleotide 576 in SEQ ID NO. 1 (64 base pairs distant from the start codon). The cDNA insert was isolated from this by restriction with SalI and SacI and cloned into the likewise cleaved vector for recombination in the vaccinia virus system. The resulting plasmid (pBP1MP52s) was deposited on May 24th 1994 at the DSM (deposit number 9217) and used for the production of recombinant Vaccinia viruses. For this up to 80% confluent 143B cells (HuTk, ATCC CRL 8303) in 35 mm culture dishes were infected with Vaccinia wild-type virus in 2 ml PBS for 30 minutes at room temperature while shaking occasionally (1 virus per 10 cells). After aspirating the supernatant and adding 2 ml culture medium (MEM, Gibco BRL #041-01095), it was incubated for 2 hours at 37° C. The medium was subsequently removed and transformation of these cells was achieved with 100 ng pBP1MP52s, 2 µg carrier DNA (calf thymus, Boehringer Mannheim #104175) and 10 µl Lipofectin (Gibco BRL #18292-011) in 1 ml MEM for 15 hours at 37° C. After addition of 1 ml MEM containing 20% FCS (Gibco BRL #011-06290), they were incubated for a further 24 hours at 37° C. and subsequently the lysed cells were frozen.

The gpt selection for xanthine-guanine phosphoribosyl transferase and isolation and amplification of individual recombinant viruses was essentially carried out as described in unit 16.17 of CP except that RK13 cells (ATCC CCL 37) were used.

Integration of MP52 cDNA into the virus genome was confirmed by dot blot and Southern blot analysis (CP unit 16.18). A recombinant virus was used for expression analyses in the cell line 143B (HuTk-, ATCC CRL 8303, human). Confluent cells were infected for 45 minutes at 37° C. with a number of viruses corresponding to the number of cells and subsequently added to the respective culture medium (MEM, Gibco BRL #041-01095) containing 10% FCS and penicillin/streptomycin (1:500, Gibco BRL #043-05140H). After 6 hours at 37° C., the medium was removed, the cells were washed twice with e.g. HBSS (Gibco BRL #042-04180M) and production medium (e.g. MEM) without FCS was added. After 20 to 22 hours of production the cell supernatant was collected. The expression was analysed by means of Western blots according to standard methods (CP unit 10.8). For this the proteins from 100 to 500 µl cell culture supernatant were precipitated by addition of an equivalent volume of acetone and incubating for at least one hour on ice and centrifuged. After resuspending the pellet in application buffer (7 M urea, 1% SDS, 7 mM sodium dihydrogen phosphate, 0.01% bromophenol blue and if desired 1% β-mercaptoethanol) separation was carried out in 15% polyacrylamide gels. A prestained protein molecular weight standard (Gibco BRL #26041-020) was used as the marker proteins. Transfer onto a PVDF membrane (Immobilon #IPVH00010) and blocking the membrane were carried out according to standard methods.

In order to detect MP52 on the membrane, polyclonal antibodies against MP52 had been produced in chickens as well as in rabbits. For this the mature part of MP52 with 6 histidines at the N-terminus was expressed in *E. coli* and purified as described for example in Hochuli et al. (BIO/Technology, Vol. 6, 1321–1325 (1988)). Both antibodies enable the specific detection of expression of MP52 wherein dimeric MP52 is less efficiently recognized than monomeric. Chicken antibodies were used for the Western blot in FIG. 3 that had been specifically purified by means of PEG precipitation (Thalley et al., BIO/Technology vol. 8 934–938 (1990)) and by means of membrane-bound antigen (mature MP52 containing 6 histidines) (18.17 in Sambrook et al., Molecular cloning, second edition, Cold Spring Harbor Laboratory Press 1989). Anti-chicken IgG with coupled alkaline phosphatase (Sigma A9171) was used as the second antibody. The detection was carried out using the Tropix Western-Light protein detection kit (Serva #WL10RC) according to the manufacturer's instructions.

The Western blot in FIG. 3 shows that MP52-specific bands only occur with the recombinant viruses but not with the wild-type viruses (without integrated foreign-DNA). The expression of MP52 results in a secreted protein having an apparent molecular weight of about 25 kDa in the gel under non-reducing conditions. The protein migrates in the gel at 14 to 15 kDa under reducing conditions. These results show that MP52 is expressed as a dimeric mature protein. The weak bands appearing in the region above 60 kDa that occur in the Western blot are probably residues of the uncleaved precursor proteins. The migration properties also confirms the theoretical molecular weights that can be derived from SEQ ID NO. 2 according to which mature, monomeric MP52 has a size of 13.6 kDa.

It has been proven to be possible to express MP52 and cleave the precursor protein to mature MP52 in various cell lines. C127 (ATCC CRL 1616, mouse), BHK21 (ATCC CCL 10, hamster), MRC-5 (ATCC CCL 171, human) and 3T6-Swiss albino (ATCC CCL 96, mouse) cells were tested.

Expression and cleavage to form mature MP52 was also demonstrated in a further eukaryotic expression system. For this cDNA from MP52 (starting with nucleotide 576) was cloned into the expression plasmid pSG5 (Stratagene #216201). The plasmid pSK52s was restricted with ClaI and XbaI and the protruding ends of the MP52 insert were made blunt by T4 polymerase treatment. Cloning into the vector pSG5, that had been restricted with EcoRI and likewise blunt ended by T4 polymerase treatment, was carried out according to standard methods. All enzymatic reactions were carried out according to the instructions of the manufacturer. Correct orientation of the MP52 insert was ensured by restriction analysis and sequencing with the T7 primer (Stratagene #300302). The resulting plasmid pSG52s (deposited on 17.05.94 at the DSM with the deposit number DSM 9204) can be cotransformed with a vector that codes for a selectable marker such as e.g. the gene for G418 resistance in order to obtain stable cell lines. For this purpose pSG52s was cotransformed with the plasmid p3616 (deposited on 17.05.94 at the DSM with the deposit number DSM 9203) in L929 cells (ATCC CCL1, mouse) using Lipofectin (Gibco BRL #18292-011) according to the manufacturer's instructions. Selection with G418 was carried out according to methods familiar to a person skilled in the art (CP, unit 9.5) and it resulted in a cell line that produced detectable mature MP52 in the Western blot.

Figure 4:
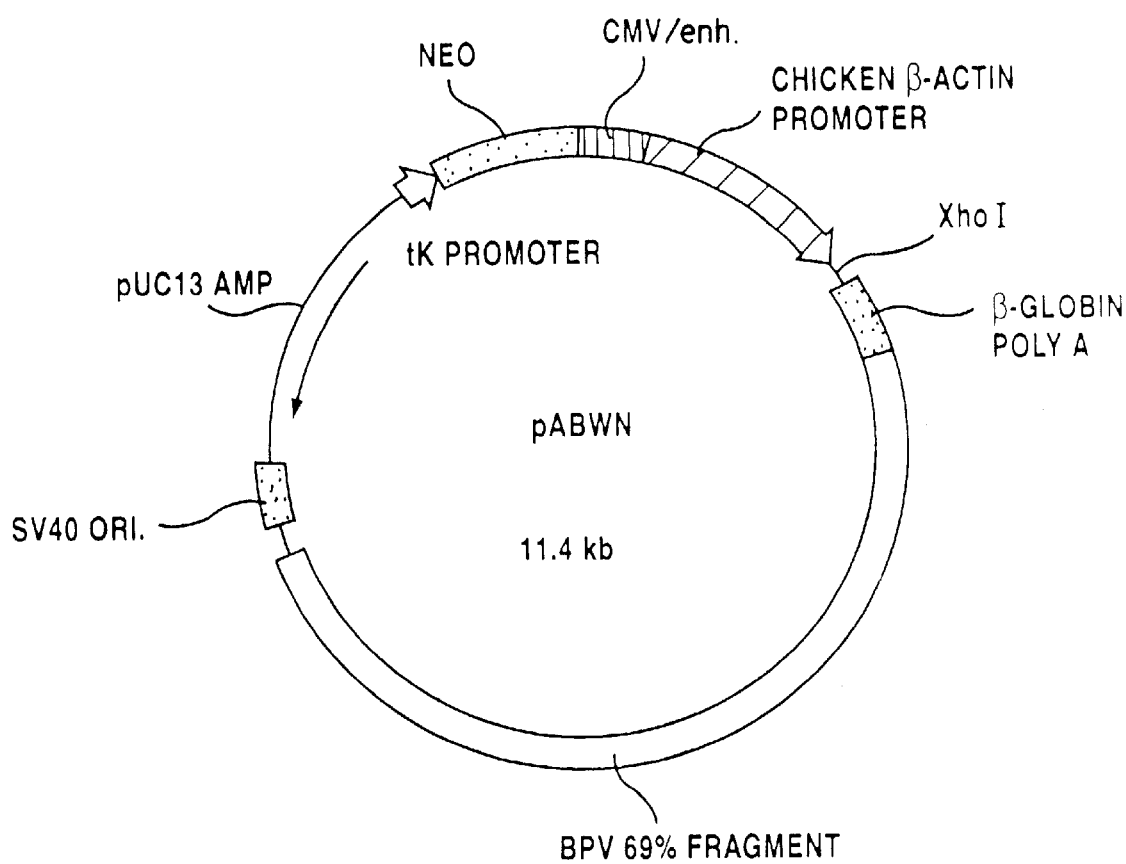

A further expression vector for MP52 was produced using the plasmid PABWN (Niwa et al., Gene 108 (1991), 193–200 and FIG. 4) which was provided by Dr. Miyazaki.

For this the HindIII fragment from plasmid pSK52s that starts with nucleotide 576 in SEQ ID NO. 1, was isolated and the protruding ends were made blunt by treatment with Klenow fragment. A Not I restriction cleavage site was introduced at both ends of the fragment by ligation of the adapter. Adapter: [SEQ ID NO. 12] AGCGGCCGCTTCGCCGGCGA Vector pABWN was restricted with XhoI, also treated with the Klenow fragment and dephosphorylated with intestinal alkaline phosphatase from the calf (Boehringer Mannheim). The same phosphorylated adapter was ligated on so that an insertion of the MP52 fragment after restriction with NotI into the generated Not I cleavage site of the vector was now possible. The expression vector that results is subsequently denoted HindIII-MP52/pABWN. All the reactions carried out for the cloning were carried out according to standard methods (e.g. CP unit 3.16).

The structure of the HindIII-MP52/pABWN expression vector was confirmed by sequencing and restriction mapping. HindIII-MP52/pABWN contains the MP52 sequence starting with nucleotide 576 and ending with nucleotide 2278 in SEQ ID NO. 1.

HindIII-MP52/pABWN was transfected in L cells* (mouse fibroblasts) and stable transformants were established therefrom.

For this 4 µg in each case of the plasmids (HindIII-MP52/pABWN or pABWN) were transfected in $5 \times 10^5$ L cells in a 6 cm culture dish using 20 µl lipofectAMINE reagent (Gibco BRL #18324-012). For this solution A (4 µg of the respective DNA in 200 µl OPTI-MEM I (Gibco BRL #31985)) was carefully mixed with solution B (20 µl lipofectAMINE reagent in 200 µl OPTI-MEM I) and incubated for 45 minutes at room temperature to form the DNA liposome complex. In the course of this the cells were washed once with 2 ml OPTI-MEM I. For each transfection, 1.6 ml OPTI-MEM I was added to the vessel with the DNA liposome complex. The solution was carefully mixed and the washed cells were overlayed therewith. The cells were incubated with the dilute complex for 5 hours at 37° C. in an $CO_2$ incubator. After the incubation 2 ml DMEM (Gibco BRL, Dulbecco's modified eagle medium)/20% FCS was added. 24 hours after the transfection, the medium was replaced with fresh DMEM/10% FCS. 48 hours after the start of transfection, the cells were transferred into a 10 cm culture dish. 72 hours after the start of the transfection, the G418 selection was started at a concentration of 800 µg/ml. The stable clones appeared after 1 to 2 weeks.

5 ml conditioned DMEM with or without FCS was obtained from confluent transformants which had been grown for 3 days in a 10 cm culture dish. The two different cell culture supernatants (HindIII-MP52/pABWN and pABWN) of transfected cells as well as cell lysates were examined by Western blot. In this process mature MP52 was found in conditioned medium as well as in cell lysates of cells transfected with HindIII-MP52/pABWN. The clones were further cloned and cells producing MP52 were each selected after Western blot analysis. Estimations from Western blot analyses yielded a MP52 production of up to 1 mg/l.

EXAMPLE 3
Biological activity of MP52

Several experiments were carried out in vitro and in vivo in order to detect the biological activity of MP52 and to prove the usefulness of this invention for medical applications for the prevention and/or treatment of bone diseases.

1. In vitro assays 1.1

Since an increase in glycosaminoglycan (GAG) synthesis is described in chondrocytes after stimulation with TGF-β (Hiraki et al., Biochimica et Biophysica Acta 969 (1988), 91–99), it was examined whether MP52 also has this influence. The chondrogenic activity of MP52 was tested in primary cultures from foetal rat extremities using the cell culture supernatants (DMEM containing 10% FCS) of L cell transformants producing MP52 (transfected with HindIII MP52/pABWN).

The four extremities of 16-day-old rat foetuses were used for this. After trypsination, the cells obtained in F-12 medium (Nutrient mixture Ham's F-12, Gibco BRL #21700) containing 10% FCS were plated out at $3 \times 10^5$ cells on 24-well plates coated with collagen type I and cultured for ca. 2 days until confluence. 56 μl conditioned medium (CM) of HindIII-MP52/pABWN-L cell transfectants, of pABWN-L cell transfectants or only medium (DMEM containing 10% FCS) was added to 500 μl culture medium in each case (F-12 medium containing 10% FCS). F-12 medium containing 10% FCS as well as the respective additives was used over a period of 0, 3, 6 and 9 days. The medium containing the respective additives was exchanged every three days. Afterwards the culture was cultured for a further 2 days in F-12 medium without FCS in the presence of the respective additives (conditioned medium or control medium) and then $^{35}$S sulfate was added for 6 hours. $^{35}$S incorporated into polysaccharides was measured after pronase E digestion and precipitation as described in Hiraki et al. (Biochimica et Biophysica Acta 969 (1988), 91–99).

TABLE 1

| | Radioactivity (cpm/well) | | |
|---|---|---|---|
| Number of days of incubation | DMEM (10% FCS) from control L cells | CM from pABWN-L cell transfectants | CM from HindIII-MP52/pABWN-L cell transfectants |
| 2 | 3720 ± 114 | 3865 ± 120 | 4879 ± 422 |
| 5 | 4188 ± 135 | 4154 ± 29 | 8223 ± 275* |
| 8 | 3546 ± 160 | 3310 ± 115 | 9890 ± 1260* |
| 11 | 3679 ± 218 | 3633 ± 167 | 7520 ± 160* |

Values relate to ± S.E.M. for 3 or 4 culture mixtures
*:p < 0.01 vs DMEM and CM from pABWN-L cell transfectants (Scheffe's multiple t-test)

As shown in Table 1, the cell culture supernatants of the transfectants producing MP52 significantly stimulate GAG synthesis in comparison to pure culture medium (DMEM containing 10% FCS) or to the cell culture supernatant from L cells transfected with pABWN. This shows that MP52 can stimulate differentiation of chondrocytes.

1.2

An effect which has been described for some members of the BMP family is the stimulation of alkaline phosphatase (ALP) activity in osteoblasts. The clonal rat cell line ROB-C26 (C-26) is among the osteoblasts at a relatively early stage of maturation (Yamaguchi et al, Calcif. Tissue Int. 49 (1991), 221–225). The capability of stimulating ALP activity is described for osteoinductive proteins such as e.g. BMP-2 by Yamaguchi et al. (J. Cell Biol. 113 (1991), 681–687).

The influence of MP52 on C26 cells was examined as follows: C26 cells were plated out at $3 \times 10^4$ cells per well in a 24-well plate and cultured in a-MEM (Gibco BRL)/10% FCS until confluence. 56 μl of the cell culture supernatant from L cell transfectants producing MP52 (Hind III-MP52/pABWN) or of the cell culture supernatant from PABWN-L cell transfectants or only of the cell culture supernatant (DMEM containing 10% FCS) from L cells was added to 500 μl of the C-26 cell culture medium. A change of medium with the respective additives was carried out every three days. The ALP activity in the cell extracts was determined after 0, 3, 6, 9 and 12 days with the aid of standard techniques based on p-nitrophenyl phosphate as the substrate as described for example by Takuwa et al. (Am. J. Physiol. 257 (1989), E797–E803).

TABLE 2

| | ALP activity (nmol/min) per well | | |
|---|---|---|---|
| Number of incubation days | DMEM (10% FCS) from control L cells | CM from pABWN-L cell transfectants | CM from HindIII-MP52/pABWN-L cell transfectants |
| 0 | 41.8 ± 2.8 | 41.8 ± 2.8 | 41.8 ± 2.8 |
| 3 | 136.3 ± 3.7 | 125.8 ± 2.3 | 181.3 ± 14.2* |
| 6 | 129.0 ± 7.8 | 119.3 ± 6.4 | 258.0 ± 8.3* |
| 9 | 118.4 ± 3.7 | 110.1 ± 2.8 | 258.4 ± 10.6* |
| 12 | 121.2 ± 3.2 | 125.3 ± 6.0 | 237.8 ± 11.0* |

Values relate to ± S.D. for 4 culture mixtures.
*:p < 0.01 vs DMEM and CM from pABWN-L cell transfectants (Scheffe's multiple t-test)

As shown in Table 2, addition of MP52 leads to a significant increase in ALP activity compared to pure DMEM/10% FCS medium and medium from pABWN-infected L cells. This result shows that MP52 cannot only cause chondrocytes to differentiate but can also lead to the differentiation and maturation of osteoblasts.

A further osteoblast cell line (MC3T3-E1, mouse) that shows an increase in the ALP activity by treatment with BMP-2 as described by Takuwa et al. (Biochem. Biophys. Res. Com. 174 (1991), 96–101), does not result in any change in the ALP activity after incubation with conditioned medium from L cell transfectants producing MP52 (HindIII-MP52/pABWN) or medium after MP52 production by infection with recombinant Vaccinia viruses. This indicates that MP52 has a cell specificity that partially deviates from that of BMP-2. Different functions due to different target sites for the individual TGF-β family members may be of great medical relevance.

2. In vivo experiments 2.1

The most definitive possibility of examining bone development is based on ectopic bone formation in vivo. This can for example be induced by implantation of demineralized bone matrix (Urist, Science 150 (1965), 893–899). The same process can be induced by combination of inactive matrix with bone-inducing proteins as described for example by Sampath et al. (PNAS* Proc.Natl.Acad.Sci. USA 78 (1981), 7599–7603). This process of bone formation is similar to embryonic enchondral bone formation and adult bone healing. This method therefore enables proteins to be examined for their bone-inductive capability in vivo.

MP52 protein which had been obtained by expression in the Vaccinia system (see example 2) was partially purified and implanted for such an experiment.

For this 143B cells (HuTk, ATCC CRL 8303) were cultured in culture dishes and roller flasks until confluence and infected with recombinant viruses as described in example 2 for the expression analyses, they were washed and MP52 was allowed to accumulate for about 20 hours in MEM (Gibco BRL, ca 1 ml per $10^6$ cells). The same preparation was infected with wild-type viruses as a control. Cell culture supernatant (conditioned medium) from each preparation was collected and centrifuged (40000×g for 30 minutes at 4° C.). In order to remove the viruses, the supernatants were filtered over inorganic filters (0.1 µm pore size, Whatman, Anotop 25). In the course of the characterization of MP52 it was shown that this protein binds to heparin-Sepharose. This property was utilized for partial purification. For this the filtered and centrifuged, conditioned medium was brought to a final concentration of 50 mM Tris pH 7.0, 100 mM NaCl and 6 M urea and it was loaded onto a heparin column (HiTrap™, Pharmacia #17-0407-01) that uses equilibrated in buffer A (50 mM Tris pH 7.0, 100 mM NaCl and 6 M urea). The loaded column was washed with buffer A and eluted with a linear gradient to 100% buffer B (50 mM Tris pH 7.0, 600 mM NaCl and 6 M urea) at a flow rate of 0.5 ml/min within 50 min (2.5 ml per fraction). The use of urea is not absolutely necessary. MP52 elutes reproducibly mainly in 2 fractions at about 250 to 400 mM NaCl as could be examined by Western blot analysis (see example 2). Aliquots of these fractions were also examined in 15% polyacrylamide gels stained with silver according to the instructions of the manufacturer (Silver Stain-II, Daiichi #SE140000) and the fractions were pooled. The comparable fractions were also pooled after analysis in gels stained with silver after purification from conditioned medium after infection with wild-type viruses.

Further examinations on MP52 showed that MP52 also binds to hydroxyapatite. Thus it is in principle possible to achieve an additional purification by a hydroxyapatite column or to replace a heparin column by a hydroxyapatite column (e.g. BIO-RAD, Econo-pac HTP). Other methods known to a person skilled in the art are also conceivable for further purifications such as e.g. gel sieve columns, ion exchanger columns, affinity columns, metal chelate columns or columns based on hydrophobic interactions.

The MP52 protein prepurified by heparin-Sepharose chromatography or the corresponding proteins that are still contaminated which are also present in the cell culture supernatants infected with the wild-type, were further purified by means of reversed phase HPLC. For this a C8 column (Aquapore RP300, Applied Biosystems, particle size: 7 µm, pore size: 300 Å) was equilibrated with 10% buffer B (buffer A: 0.1% trifluoroacetic acid; buffer B: 90% acetonitrile, 0.1% trifluoroacetic acid). After loading the column with the pooled fractions containing MP52 from the heparin column it was extensively washed with 10% buffer B. The bound protein was eluted with the following gradient: 10 to 50% buffer B for 20 minutes and 50 to 100% buffer B for 50 minutes. Fractions of 500 µl were collected and analysed by Western blot as well as with gels stained with silver. The MP52 protein elutes under the selected conditions in the range of about 55 to 65% acetonitrile. The fractions containing MP52 were pooled. The same procedure was carried out with the corresponding fractions from the control purification of cell culture supernatant from cells infected with wild-type viruses.

Partially purified MP52 protein at a concentration estimated to be 50 ng/ml according to Western blot analysis also showed a significant increase in the ALP activity in ROB-C26 cells after three days of incubation.

Partially purified MP52 protein or control protein from the corresponding partially purified cell culture supernatants after infection with wild-type viruses were reconstituted with matrix and implanted in rats in order to prove its capability for cartilage and bone formation.

In principle various matrix materials known to a person skilled in the art should be usable i.e. natural (also modified) and synthetically prepared matrices, however, biocompatible porous materials that can be biologically degraded are preferred. In these experiments bone matrix from rats was used that had been prepared essentially in a similar way to that described by Sampath et al. (PNAS 80 (1983), 6591–6595). The rat bones (femur and tibia) were demineralized in 0.6 M HCl for 24 hours and subsequently bone marrow that was still present was removed. After washing with water and defatting for three hours in a chloroform/methanol (1/1) mixture, the bones were air-dried, powderized in a mill in a deep-frozen state and particle sizes between 400 and 1000 µm were sieved out. Subsequently the matrix was extracted for 7 days at room temperature in 4 M guanidinium HCl in the presence of protease inhibitors. After washing extensively with water, the matrix was lyophilized and stored at 4° C. Matrices treated in this way do not on their own show bone-inducing activity.

Protein can be combined with the extracted bone matrix by various methods known to a person skilled in the art. MP52 protein or control protein that had been purified by means of heparin-Sepharose as well as by reversed phase HPLC, was combined after elution in the acetonitrile/trifluoro-acetic acid solution with 25 mg matrix in each case per implant, mixed well, deep-frozen and lyophilized.

For the implantation of matrix-bound MP52, two ca. 3 months-old rats (Whistar) were used which had been anaesthetised by intramuscular injection of an anaesthetic (0.2 ml Rompun (Bayer) mixed with 0.5 ml Ketanest 50 (Parke Davis)) using 0.14 ml per 100 g body weight. Bilateral pockets were prepared in the abdominal muscles for the implants (beneath the thorax, starting ca. 0.5 cm below the lowest costal arch). The matrix-bound MP52 (ca. 2 to 4 µg as estimated by Western blot) as well as the corresponding matrix-bound control proteins were moistened using 0.9% saline solution (Delta Pharma) and introduced into the muscular pockets. The muscular pockets as well as the necessary skin incisions were subsequently sutured. The rats were immunosuppressed with Cyclosporin A (Sandimmun).

Figure 5:
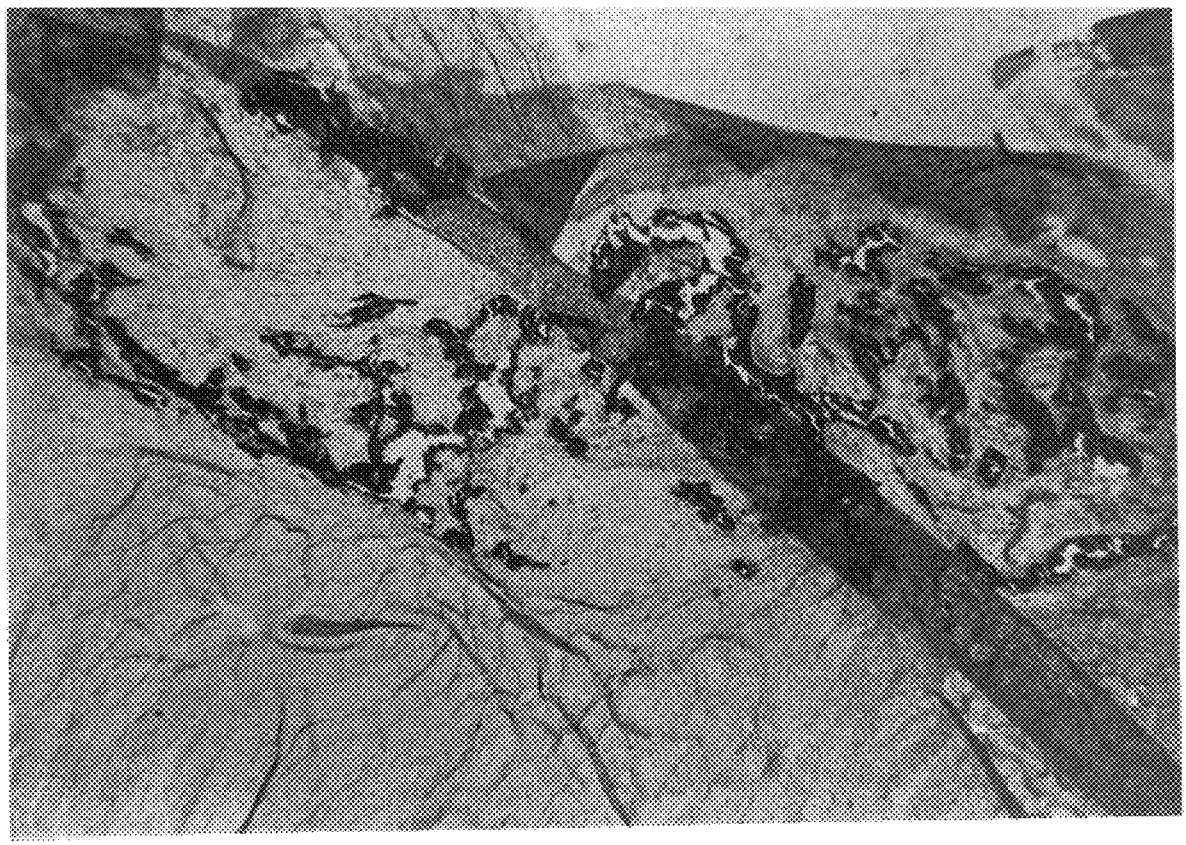
Figure 6:
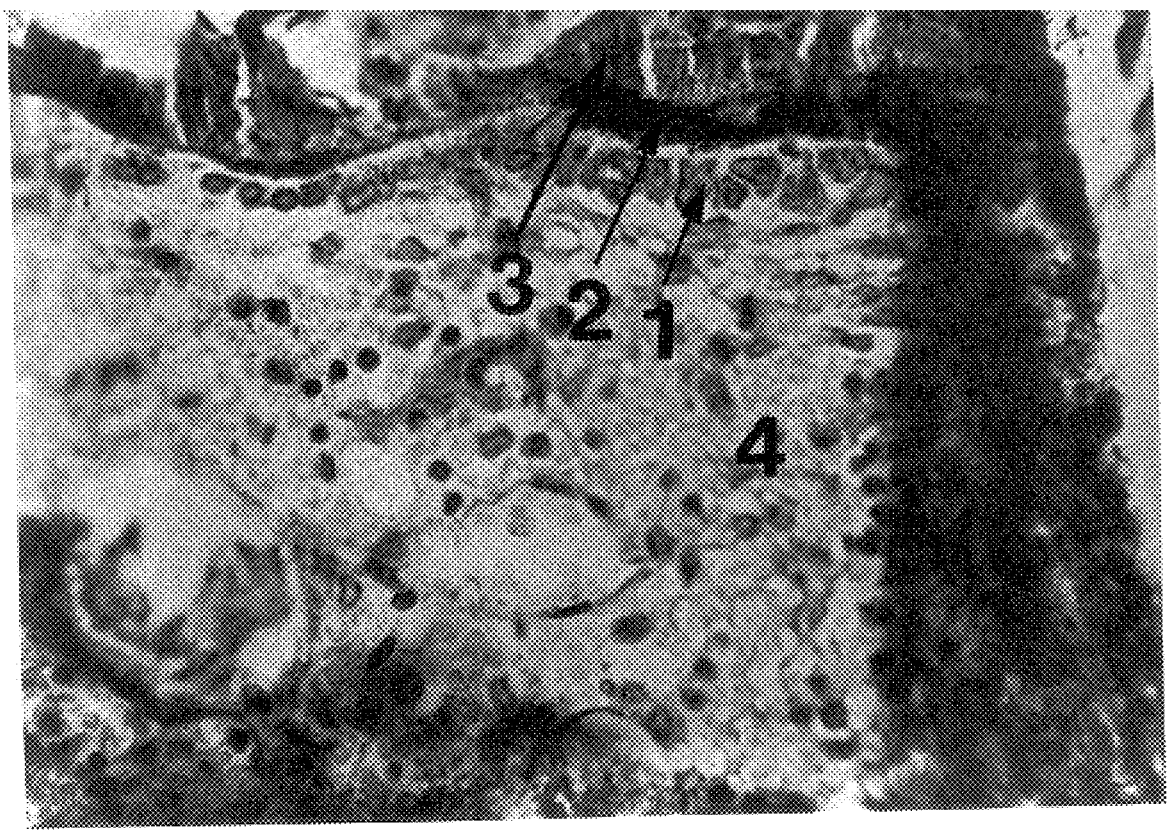

After 18 or after 26 days the implants were removed from the rats and fixed for histological examinations. Since after 26 days the implant with MP52 allowed the assumption that macroscopically bone formation had already occurred, this was embedded in methylmeth-acrylate in order to prepare thin sections, the other implants were embedded in paraffin. Mineralized cartilage and bone tissues are accentuated in black by means of the von Kossa staining technique (Romeis, B.; "Mikroskopische Technik", Ed: Böck, P.; Urban and Schwarzenberg; Munich, Baltimore, Vienna (1989)). In the trichromium staining according to Masson-Goldner (Romeis, B.; "Mikroskopische Technik", Ed: Böck, P.; Urban and Schwarzenberg; Munich, Baltimore, Vienna (1989)), mineralized bone tissue and collagen are stained bright green, osteoid is stained red and cytoplasm reddish-brown. Both staining techniques were used on implants from both rats. In both experimental animals considerable formation of cartilage and bone was detected in the implants containing MP52 using both staining techniques. The corresponding implants with control protein showed no formation whatsoever of cartilage or bone. The number of cartilage precursors with chondrocytes and cartilage areas with initial formation of extracellular matrix and its mineralization in concentric circles is higher in the MP52 implant after 18 days than in the one after 26 days. Mature bone tissue with vectorial osteoid formation as well as individual osteocytes in the bone is, however, also detectable in the implant after 18 days. In addition closed ossicles can be observed with the onset of bone marrow formation. In the implant after 26 days areas of cartilage with initial matrix formation and calcification are also detectable, the portion of mineralized bone tissue stained green and having osteocytes and osteoid edges has, however, significantly increased. In this implant bone marrow formation together with the occurrence of isolated fat cells can also be detected. For illustration FIG. 5 shows the staining test of the bone material (according to von Kossa stain.) from the entire implant after 26 days. A small section of the same implant is shown in FIG. 6 after staining according to Masson-Goldner. It shows active bone with an edging of cuboidal osteoblasts and osteoid in which individual embedded osteoblasts can be recognized. Furthermore individual osteocytes can also be seen in the mineralized bone tissue (stained green in the original preparation). The formation of bone marrow is also detectable.

The experiment shows that recombinantly produced MP52 alone, in combination with a matrix is capable of inducing enchondral bone formation.

2.2

In order to confirm the results, a further ectopic test for bone formation using MP52 L cell transformants was carried out. L cells (1×10⁶ cells) producing MP52 (transfected with HindIII-MP52/pABWN) and non-producing (pABWN-transfected) L cells were injected into the bilateral thigh muscles of three male naked mice in each case. All animals were killed after three weeks, the thigh muscles were excised and these were examined with low energy X-ray radiation as well as histopathologically.

Analysis by X-ray radiation shows dense material at the injection sites in the muscle tissue of all L cells producing MP52 as listed in Table 3. Simple cartilage formation and calcified cartilage formation could be determined in the muscles using histological examinations. These results also confirm that MP52 can induce enchondral bone formation.

TABLE 3

|  | Cells producing MP52 (HindIII-MP52/pABWN) | Control cells (pABWN) |
| --- | --- | --- |
| dense material by X-ray analysis | 3/3 | 0/3 |
| chondrocytes by histology | 3/3 | 0/3 |
| calcified cartilage formation by histology | 3/3 | 0/3 |

The experiments that were carried out confirm that MP52 protein stimulates the formation of cartilage from undifferentiated mesenchymal cells as well as the differentiation and maturation of osteoblasts. This leads to enchondral bone formation which is similar to the induction cascade in embryonic bone formation and bone healing of fractures.

The conditions stated in the experiments are to be looked upon as an illustration of the MP52 activity but not as limitation. The invention can also be examined and characterized in another form.

We claim:

1. An isolated DNA molecule which codes for a protein of the TGF-β family, wherein said DNA molecule comprises a sequence selected from the group consisting of:
   a) the sequence shown in SEQ ID NO:1,
   b) a part of SEQ ID NO:1 which encodes the mature protein,
   c) a nucleotide sequence which encodes the amino acid sequence according to SEQ ID NO:2,
   d) a nucleotide sequence which encodes a portion of the amino acid sequence according to SEQ ID NO:2, wherein said portion is the mature protein, and
   e) a part of SEQ ID NO:1 which encodes the amino acid sequence according to SEQ ID NO:13.

2. The DNA molecule according to claim 1, wherein said DNA molecule is the part of SEQ ID NO:1 which encodes the mature protein and further comprises nucleotide sequences coding for functional signal and/or propeptide sequences from a protein of the TGF-β family.

3. The DNA molecule according to claim 2, wherein said functional signal and/or propeptide sequences of said DNA molecule are the functional signal and/or propeptide sequences of SEQ ID NO:2.

4. The DNA molecule according to claim 3, further comprising a non-coding intron between nucleotides 1270 and 1271 of SEQ ID NO:1.

5. The DNA molecule according to claim 1, wherein said DNA molecule comprises nucleotides 640–2142 of SEQ ID NO:1.

6. A vector comprising at least one copy of a DNA molecule according to claim 1.

7. A host cell transformed by a vector according to claim 6.

8. The host cell according to claim 7, wherein said host cell is selected from the group consisting of a bacterium, a fungal cell, a plant cell, and an animal cell.

9. A process for the production of a protein of the TGF-β family, comprising the steps of:

culturing a host cell according to claim 7 in a culture media, and isolating TGF-β protein from said host cell or from said culture media.

10. An isolated DNA molecule comprising nucleotide sequences coding for the functional signal and/or propeptide sequence of SEQ ID NO:2.

* * * * *

UNITED STATES PATENT AND TRADEMARK OFFICE
CERTIFICATE OF CORRECTION

PATENT NO. : 5,994,094
DATED : November 30, 1999
INVENTOR(S) : HOTTEN et al

It is certified that error appears in the above-indentified patent and that said Letters Patent is hereby corrected as shown below:

Column 4, line 48, please delete "MOCOS" and insert --MO, COS--

Column 5, line 21, please delete "chirgwin" and insert --Chirgwin--

Column 6, line 52, please delete "MRNA" and insert --Mrna--

Column 7, line 39, please delete "CDNA" and insert --cDNA--

Column 8, line 4, please delete "CDNA" and insert --cDNA--

Column 9, lines 62 and 67, please delete "17.05.94" and insert --05.17.94--

Column 10, line 8, please delete "PABWN" and insert --pABWN--

Column 10, line 15, please delete "[SEQ ID NO. 12] AGCGGCCGCTTCGCCGGCGA and insert --[SEQ ID NO. 12] AGCGGCCGCT TCGCCGGCGA--

Column 12, line 6, please delete "PABWN-L" and insert --pABWN-L--

UNITED STATES PATENT AND TRADEMARK OFFICE
CERTIFICATE OF CORRECTION

PATENT NO. : 5,994,094
DATED : November 30, 1999
INVENTOR(S) : HOTTEN et al

It is certified that error appears in the above-indentified patent and that said Letters Patent is hereby corrected as shown below:

Column 14, line 48, please delete "methylmeth-acrylate" and insert --methylmethacrylate--

Signed and Sealed this

Twenty-seventh Day of March, 2001

Attest:

NICHOLAS P. GODICI

Attesting Officer    Acting Director of the United States Patent and Trademark Office

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 2703 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

```
CCATGGCCTC GAAAGGGCAG CGGTGATTTT TTTCACATAA ATATATCGCA CTTAAATGAG      60

TTTAGACAGC ATGACATCAG AGAGTAATTA AATTGGTTTG GGTTGGAATT CCGTTTCCAA     120

TTCCTGAGTT CAGGTTTGTA AAAGATTTTT CTGAGCACCT GCAGGCCTGT GAGTGTGTGT     180

GTGTGTGTGT GTGTGTGTGT GTGTGTGTGA AGTATTTTCA CTGGAAAGGA TTCAAAACTA     240

GGGGGAAAAA AAAACTGGAG CACACAGGCA GCATTACGCC ATTCTTCCTT CTTGGAAAAA     300

TCCCTCAGCC TTATACAAGC CTCCTTCAAG CCCTCAGTCA GTTGTGCAGG AGAAAGGGGG     360

CGGTTGGCTT TCTCCTTTCA AGAACGAGTT ATTTTCAGCT GCTGACTGGA GACGGTGCAC     420

GTCTGGATAC GAGAGCATTT CCACTATGGG ACTGGATACA AACACACACC CGGCAGACTT     480

CAAGAGTCTC AGACTGAGGA GAAAGCCTTT CCTTCTGCTG CTACTGCTGC TGCCGCTGCT     540

TTTGAAAGTC CACTCCTTTC ATGGTTTTTC CTGCCAAACC AGAGGCACCT TTGCTGCTGC     600
```

```
CGCTGTTCTC TTTGGTGTCA TTCAGCGGCT GGCCAGAGGA TGAGACTCCC CAAACTCCTC       660

ACTTTCTTGC TTTGGTACCT GGCTTGGCTG GACCTGGAAT TCATCTGCAC TGTGTTGGGT       720

GCCCCTGACT TGGGCCAGAG ACCCCAGGGG ACCAGGCCAG GATTGGCCAA AGCAGAGGCC       780

AAGGAGAGGC CCCCCCTGGC CCGGAACGTC TTCAGGCCAG GGGGTCACAG CTATGGTGGG       840

GGGGCCACCA ATGCCAATGC CAGGGCAAAG GGAGGCACCG GCAGACAGG AGGCCTGACA        900

CAGCCCAAGA AGGATGAACC CAAAAAGCTG CCCCCCAGAC CGGGCGGCCC TGAACCCAAG       960

CCAGGACACC CTCCCCAAAC AAGGCAGGCT ACAGCCCGGA CTGTGACCCC AAAAGGACAG      1020

CTTCCCGGAG GCAAGGCACC CCCAAAAGCA GGATCTGTCC CCAGCTCCTT CCTGCTGAAG      1080

AAGGCCAGGG AGCCCGGGCC CCCACGAGAG CCCAAGGAGC CGTTTCGCCC ACCCCCCATC      1140

ACACCCCACG AGTACATGCT CTCGCTGTAC AGGACGCTGT CCGATGCTGA CAGAAAGGGA      1200

GGCAACAGCA GCGTGAAGTT GGAGGCTGGC CTGGCCAACA CCATCACCAG CTTTATTGAC      1260

AAAGGGCAAG ATGACCGAGG TCCCGTGGTC AGGAAGCAGA GGTACGTGTT TGACATTAGT      1320

GCCCTGGAGA AGGATGGGCT GCTGGGGGCC GAGCTGCGGA TCTTGCGGAA GAAGCCCTCG      1380

GACACGGCCA AGCCAGCGGC CCCCGGAGGC GGGCGGGCTG CCCAGCTGAA GCTGTCCAGC      1440

TGCCCCAGCG GCCGGCAGCC GGCCTCCTTG CTGGATGTGC GCTCCGTGCC AGGCCTGGAC      1500

GGATCTGGCT GGGAGGTGTT CGACATCTGG AAGCTCTTCC GAAACTTTAA GAACTCGGCC      1560

CAGCTGTGCC TGGAGCTGGA GGCCTGGAA CGGGGCAGGG CCGTGGACCT CCGTGGCCTG      1620

GGCTTCGACC GCGCCGCCCG GCAGGTCCAC GAGAAGGCCC TGTTCCTGGT GTTTGGCCGC      1680

ACCAAGAAAC GGGACCTGTT CTTTAATGAG ATTAAGGCCC GCTCTGGCCA GGACGATAAG      1740

ACCGTGTATG AGTACCTGTT CAGCCAGCGG CGAAAACGGC GGGCCCCACT GGCCACTCGC      1800

CAGGGCAAGC GACCCAGCAA GAACCTTAAG GCTCGCTGCA GTCGGAAGGC ACTGCATGTC      1860

AACTTCAAGG ACATGGGCTG GGACGACTGG ATCATCGCAC CCCTTGAGTA CGAGGCTTTC      1920

CACTGCGAGG GGCTGTGCGA GTTCCCATTG CGCTCCCACC TGGAGCCCAC GAATCATGCA      1980

GTCATCCAGA CCCTGATGAA CTCCATGGAC CCCGAGTCCA CCACCCCAC CTGCTGTGTG       2040

CCCACGCGGC TGAGTCCCAT CAGCATCCTC TTCATTGACT CTGCCAACAA CGTGGTGTAT      2100

AAGCAGTATG AGGACATGGT CGTGGAGTCG TGTGGCTGCA GGTAGCAGCA CTGGCCCTCT      2160

GTCTTCCTGG GTGGCACATC CCAAGAGCCC CTTCCTGCAC TCCTGGAATC ACAGAGGGGT      2220

CAGGAAGCTG TGGCAGGAGC ATCTACACAG CTTGGGTGAA AGGGGATTCC AATAAGCTTG      2280

CTCGCTCTCT GAGTGTGACT TGGGCTAAAG GCCCCCTTTT ATCCACAAGT TCCCCTGGCT      2340

GAGGATTGCT GCCCGTCTGC TGATGTGACC AGTGGCAGGC ACAGGTCCAG GGAGACAGAC      2400

TCTGAATGGG ACTGAGTCCC AGGAAACAGT GCTTTCCGAT GAGACTCAGC CCACCATTTC      2460

TCCTCACCTG GGCCTTCTCA GCCTCTGGAC TCTCCTAAGC ACCTCTCAGG AGAGCCACAG      2520

GTGCCACTGC CTCCTCAAAT CACATTTGTG CCTGGTGACT TCCTGTCCCT GGGACAGTTG      2580

AGAAGCTGAC TGGGCAAGAG TGGGAGAGAA GAGGAGAGGG CTTGGATAGA GTTGAGGAGT      2640

GTGAGGCTGT TAGACTGTTA GATTTAAATG TATATTGATG AGATAAAAAG CAAAACTGTG      2700

CCT                                                                   2703
```

(2) INFORMATION FOR SEQ ID NO:2:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Leu Pro Lys Leu Leu Thr Phe Leu Leu Trp Tyr Leu Ala Trp
 1               5                  10                  15

Leu Asp Leu Glu Phe Ile Cys Thr Val Leu Gly Ala Pro Asp Leu Gly
             20                  25                  30

Gln Arg Pro Gln Gly Thr Arg Pro Gly Leu Ala Lys Ala Glu Ala Lys
         35                  40                  45

Glu Arg Pro Pro Leu Ala Arg Asn Val Phe Arg Pro Gly Gly His Ser
 50                  55                  60

Tyr Gly Gly Gly Ala Thr Asn Ala Asn Ala Arg Ala Lys Gly Gly Thr
 65                  70                  75                  80

Gly Gln Thr Gly Gly Leu Thr Gln Pro Lys Lys Asp Glu Pro Lys Lys
                 85                  90                  95

Leu Pro Pro Arg Pro Gly Gly Pro Glu Pro Lys Pro Gly His Pro Pro
             100                 105                 110

Gln Thr Arg Gln Ala Thr Ala Arg Thr Val Thr Pro Lys Gly Gln Leu
         115                 120                 125

Pro Gly Gly Lys Ala Pro Pro Lys Ala Gly Ser Val Pro Ser Ser Phe
130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                 165                 170                 175

Tyr Arg Thr Leu Ser Asp Ala Asp Arg Lys Gly Gly Asn Ser Ser Val
                 180                 185                 190

Lys Leu Glu Ala Gly Leu Ala Asn Thr Ile Thr Ser Phe Ile Asp Lys
             195                 200                 205

Gly Gln Asp Asp Arg Gly Pro Val Val Arg Lys Gln Arg Tyr Val Phe
210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                 245                 250                 255

Gly Gly Arg Ala Ala Gln Leu Lys Leu Ser Ser Cys Pro Ser Gly Arg
             260                 265                 270

Gln Pro Ala Ser Leu Leu Asp Val Arg Ser Val Pro Gly Leu Asp Gly
             275                 280                 285

Ser Gly Trp Glu Val Phe Asp Ile Trp Lys Leu Phe Arg Asn Phe Lys
290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                 325                 330                 335

His Glu Lys Ala Leu Phe Leu Val Phe Gly Arg Thr Lys Lys Arg Asp
             340                 345                 350

Leu Phe Phe Asn Glu Ile Lys Ala Arg Ser Gly Gln Asp Asp Lys Thr
             355                 360                 365

Val Tyr Glu Tyr Leu Phe Ser Gln Arg Arg Lys Arg Arg Ala Pro Leu
370                 375                 380

Ala Thr Arg Gln Gly Lys Arg Pro Ser Lys Asn Leu Lys Ala Arg Cys
385                 390                 395                 400
```

```
Ser Arg Lys Ala Leu His Val Asn Phe Lys Asp Met Gly Trp Asp Asp
            405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

AGAATTCGCA TGCCATGGTC GACG          24

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CTTGAGTACG AGGCTTTCCA CTG          23

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ATTCGCATGC CATGGTCGAC GAAG          24

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GGAGCCCACG AATCATGCAG TCA          23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ACAGCAGGTG GGTGGTGTGG ACT          23

(2) INFORMATION FOR SEQ ID NO:8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AGAATTCGCA TGCCATGGTC GACGAAGCTT TTTTTTTTTT TTTT          44

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CCAGCAGCCC ATCCTTCTCC          20

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

TCCAGGGCAC TAATGTCAAA CACG          24

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ACTAATGTCA AACACGTACC TCTG          24

(2) INFORMATION FOR SEQ ID NO:12:

(i) SEQUENCE CHARACTERISTICS:

(A) LENGTH: 10 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:12:

AGCGGCCGCT                                                                               10

(2) INFORMATION FOR SEQ ID NO:13:

(i) SEQUENCE CHARACTERISTICS:
            (A) LENGTH: 102 amino acids
            (B) TYPE: amino acid
            (D) TOPOLOGY: linear (ii) MOLECULE TYPE: protein (xi) SEQUENCE DESCRIPTION: SEQ ID NO:13:

```
Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
                20                  25                  30

Leu Cys Glu Phe Pro Leu Arg Ser His Leu Glu Pro Thr Asn His Ala
            35                  40                  45

Val Ile Gln Thr Leu Met Asn Ser Met Asp Pro Glu Ser Thr Pro Pro
        50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
                100
```

(2) INFORMATION FOR SEQ ID NO:14:

(i) SEQUENCE CHARACTERISTICS:
            (A) LENGTH: 102 amino acids
            (B) TYPE: amino acid
            (D) TOPOLOGY: linear (ii) MOLECULE TYPE: protein (ix) FEATURE:
            (A) NAME/KEY: misc_feature
            (B) LOCATION: 60
            (C) OTHER INFORMATION: /note= "Xaa is a gap inserted only for
                comparison purposes"

(xi) SEQUENCE DESCRIPTION: SEQ ID NO:14:

```
Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Xaa Lys Ile Pro Lys
        50                  55                  60

Ala Cys Cys Val Pro Thr Glu Leu Ser Ala Ile Ser Met Leu Tyr Leu
65                  70                  75                  80

Asp Glu Asn Glu Lys Val Val Leu Lys Asn Tyr Gln Asp Met Val Val
                85                  90                  95
```

```
Glu Gly Cys Gly Cys Arg
            100

(2) INFORMATION FOR SEQ ID NO:15:

(i) SEQUENCE CHARACTERISTICS:
        (A) LENGTH: 102 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 60
        (C) OTHER INFORMATION: /note= "Xaa is a gap inserted only for
            comparison purposes"

(xi) SEQUENCE DESCRIPTION: SEQ ID NO:15:

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Xaa Ser Ile Pro Lys
50                  55                  60

Ala Cys Cys Val Pro Thr Glu Leu Ser Ala Ile Ser Met Leu Tyr Leu
65                  70                  75                  80

Asp Glu Tyr Asp Lys Val Leu Lys Asn Tyr Gln Glu Met Val Val
                85                  90                  95

Glu Gly Cys Gly Cys Arg
            100

(2) INFORMATION FOR SEQ ID NO:16:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:16:

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
            35                  40                  45

Ile Val Gln Thr Leu Val His Leu Met Phe Pro Asp His Val Pro Lys
50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100

(2) INFORMATION FOR SEQ ID NO:17:

(i) SEQUENCE CHARACTERISTICS:
        (A) LENGTH: 102 amino acids
```

(B) TYPE: amino acid
        (D) TOPOLOGY: linear (ii) MOLECULE TYPE: protein (xi) SEQUENCE DESCRIPTION: SEQ ID NO:17:

Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100

(2) INFORMATION FOR SEQ ID NO:18:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:18:

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
            20                  25                  30

Glu Cys Ala Phe Pro Leu Asn Ser Tyr Met Asn Ala Thr Asn His Ala
        35                  40                  45

Ile Val Gln Thr Leu Val His Phe Ile Asn Pro Glu Thr Val Pro Lys
    50                  55                  60

Pro Cys Cys Ala Pro Thr Gln Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ala Cys Gly Cys His
            100

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

ATGAATTCCC ATGGACCTGG GCTGGMAKGA MTGGAT                                          36

(2) INFORMATION FOR SEQ ID NO:20:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

ACGTGGGGTG GAATGACTGG AT                                                22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

ATATTGGCTG GAGTGAATGG AT                                                22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

ATGTGGGCTG GAATGACTGG AT                                                22

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

ACCTGGGCTG GCAGGACTGG AT                                                22

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

AGGACCTCGG CTGGAAGTGG AT                                                22

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GGGATCTAGG GTGGAAATGG AT                                                    22

(2) INFORMATION FOR SEQ ID NO:26:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

AGGATCTGGG CTGGAAGTGG GT                                                    22

(2) INFORMATION FOR SEQ ID NO:27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:27:

AGCTGGGCTG GGAACGGTGG AT                                                    22

(2) INFORMATION FOR SEQ ID NO:28:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:28:

ACATCGGCTG GAATGACTGG AT                                                    22

(2) INFORMATION FOR SEQ ID NO:29:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:29:

TCATCGGCTG GAACGACTGG AT                                                    22

(2) INFORMATION FOR SEQ ID NO:30:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:30:

ATGAATTCGA GCTGCGTSGG SRCACAGCA                                             29

-continued (2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GAGTTCTGTC GGGACACAGC A                                              21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CATCTTTTCT GGTACACAGC A                                              21

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

CAGTTCAGTG GGCACACAAC A                                              21

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

GAGCTGCGTG GGCGCACAGC A                                              21

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

CAGCGCCTGC GGCACGCAGC A                                              21

(2) INFORMATION FOR SEQ ID NO:36:

(i) SEQUENCE CHARACTERISTICS:

```
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:36:

TAAATCTTGG GACACGCAGC A                                              21

(2) INFORMATION FOR SEQ ID NO:37:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:37:

CAGGTCCTGG GGCACGCAGC A                                              21

(2) INFORMATION FOR SEQ ID NO:38:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

CCCTGGGAGA GCAGCACAGC A                                              21

(2) INFORMATION FOR SEQ ID NO:39:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

CAGCTTGGTG GGCACACAGC A                                              21

(2) INFORMATION FOR SEQ ID NO:40:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:40:

CAGCTTGGTG GGAATGCAGC A                                              21
```